United States Patent [19]

Norris et al.

[11] Patent Number: 5,030,660

[45] Date of Patent: Jul. 9, 1991

[54] INSECT REPELLENT CONTAINING 1-DODECENE

[75] Inventors: Dale M. Norris; Shao-Hua Liu, both of Madison, Wis.

[73] Assignee: Wisconsin Alumni Research Foundation, Madison, Wis.

[21] Appl. No.: 429,949

[22] Filed: Nov. 1, 1989

[51] Int. Cl.$^5$ .............................................. A01N 27/00
[52] U.S. Cl. .................................... 514/762; 514/919
[58] Field of Search ................................. 514/762, 919

[56] References Cited

U.S. PATENT DOCUMENTS

| | | | |
|---|---|---|---|
| 4,040,921 | 8/1977 | Fields | 204/158 R |
| 4,287,349 | 9/1981 | Fields | 204/158 R |
| 4,740,627 | 4/1988 | Byers et al. | 568/469.9 |
| 4,843,178 | 6/1989 | Byers et al. | 568/469.9 |

FOREIGN PATENT DOCUMENTS 2126481A 3/1984 United Kingdom .

OTHER PUBLICATIONS

Buttery et al., *J. Agric. Food Chem.*, (1984), 32, 254–256.
Gilbert et al., *J. Insect Physiol.*, (1967), 13, 1453–1459.
Gilbert and Norris, *J. Insect Physiol.*, (1968), 14, 1063–1068.
Feeny et al., *Ann. Entomol. Soc. Am.*, (1970), 63, 832–841.
Free and Williams, *J. Appl. Ecol.*, (1978), 15, 761–774.
Kamm and Buttery, *Entomol. Exp. Appl.*, (1983), 33, 129–134.
Khan et al., *J. Chem. Ecol.*, (1987), 13, 1903–1915.
Hsiao and Frankel, *Ann. Entomol. Soc. Am.*, (1968), 61, 493–503.
Buttery et al., *J. Agric. Food Chem.*, (1978), 26, 866–869.
Buttery et al., *J. Agric. Food Chem.*, (1982a), 30, 791–792.
Buttery et al., *J. Agric. Food Chem.*, (1982b), 30, 739–742.
Buttery et al., *J. Agric. Food Chem.*, (1985), 33, 772–774.
Visser and Ave, *Entomol. Exp. Appl.*, (1978), 24, 738–749.
Saxena and Prabha, *J. Entomol. Ser. A* (1975), 50, 119–126.
Ryan and Guerin, *Physiol. Entomol.*, (1982), 7, 315–324.
Salama and Saleh, *Z. Ang. Entomol.*, (1984), 97, 393–398.
Leudders and Dickerson, *Crop Sci.*, (1977), 17, 395–397.
Kahn et al., *Environ. Entomol.*, (1986a), 15, 803–808.
Kahn et al., *Entomol. Exp. Appl.*, (1986b), 42, 109–117.
Van Duyn et al., *Crop Sci.*, (1971), 11, 572–573.
Chiang et al., *Entomol. Exp. Appl.*, (1986), 42, 19–26.
G. K. Rufener, II et al., *J. Economic Entomol.*, (1986), 1979, 1354–1358.
Shorey et al., *Ann. Entomol. Soc. Am.* (1962), 55, 591–597.
Flanders, *Environ. Entomol.*, (1984), 13, 995–999.
Liu et al., *Entomol. Exp. Appl.*, (1988), 49, 99–109.
Norris et al., *Endocrinological Frontiers in Physiological Insect Ecology*, Wroclaw Tech. Univ. Press, (1988).
T. Suzuki et al., *Agr. Biol. Chem.*, (1975), 39, 2207–2211.
Shao-Hua Liu et al., *J. Agric. Food Chem.*, (1989), 37, 496–501.
Mandai et al., *Tetrahedron*, (1979), 35, 309–311.
Kul'Kova, T. A. et al., "The Effect of Altozar Altosid SR-10 And Derivatives Of Farnesylic-Acid And 3 11 DI Methyl-2 Dodecenoic-Acid On The Bug Rhodnius-Prolixus," *Med Parazitol Parazit Bolezni*, vol. 52, No. 4, 1983, pp. 46–51.
Rose et al., The Condensed Chemical Dictionary, 6th Ed., (1964).

*Primary Examiner*—Allen J. Robinson
*Attorney, Agent, or Firm*—Andrus, Sceales, Starke & Sawall

[57] ABSTRACT

An insect repellent composition containing, as an active ingredient, 1-dodecene is described. When applied to an insect or a habitat thereof, the composition is effective in deterring insects.

24 Claims, 1 Drawing Sheet

INSECT REPELLENT CONTAINING 1-DODECENE

This invention was made with U.S. Government support awarded by USDA, Grant numbers: 84-CRCR-1-1501 and 88-37153-4043 and USDA HATCH Funds. The U.S. Government has certain rights in this invention.

FIELD OF THE INVENTION

The present invention is generally directed to compositions for repelling and deterring insects. Specifically, the present invention is directed to the use of 1-dodecene as an insect repellent.

DESCRIPTION OF THE PRIOR ART

As used herein, definition of the term "insects" has been expanded to include all manner of arthropods, e.g., cockroaches, ants, bees, wasps, mosquitoes, Mexican bean beetles, biting flies, spiders, cabbage loopers, ticks, fleas and mites. Insects are often a constant source of injury and annoyance to plants and animals. While their presence alone can be annoying, they are also the source of discomfort to animals most notably by biting and stinging. These attacks can further transmit pathogens that cause serious diseases, e.g., malaria, plague, yellow fever and Lyme disease, which may be fatal. Additionally, insects can cause millions of dollars in damage to crops and other plants.

Various agents have been developed to be used as insect repellents for agricultural, gardening or other purposes. As used herein, the term "repellent" is intended to mean a composition or material which is used to drive away insects or other pests from a particular area or surface. Although a "repellent" can be an insecticide, i.e., a substance used to kill insects, it does not require that capability. Repellents have been primarily used for the prevention of breeding, biting and stinging of agricultural or sanitary insect pests. Currently, the major chemical insect repellent in commercial use is N,N-diethyl meta-toluamide (DEET). In order for DEET to remain a commercially acceptable active ingredient in repellents, it must be used at a concentration of about 14-19 volume percent (vol. %). DEET has been found to be detrimental to the health of some humans, especially children. It is therefore important to develop a composition which both solves the problems associated with safety and produces an effective insect repellent.

There have been several studies concerning the interactions between phytophagous insects and plants that emit a volatile chemical cue which evokes specific behavioral responses by the insects (Buttery, et al., *J. Agric. Food Chem.* (1984), 32, 254). Specific evidence that volatile phytochemicals play important roles in an insect's rejection or acceptance of a plant includes findings by Gilbert, et al., *J. Insect Physiol* (1967), 13, 1453; Gilbert and Norris, *J. Insect Physiol* (1968), 14, 1063; Feeny, et al., *Ann. Entomol. Soc. Am* (1970), 63, 832; Jermy, *The Host-Plant in Relation to Insect Behavior and Reproduction* (1976); Free and Williams, *J. Appl. Ecol.* (1978), 15, 761; Kamm and Buttery, *Entomol. Exp. Appl.* (1983) 33, 129; Khan, et al., *J. Chem. Ecol.* (1987), 13, 1903.

While volatiles have been reported specifically as attractants of insects to host plants (Hsiao and Frankjel, *Ann. Entomol. Soc. Am.* (1968), 61, 493; Buttery, et al. *J. Agric. Food Chem.* (1978), 26, 866; Buttery, et al., *J. Agric. Food Chem.* (1982a), 30, 791; Buttery, et al., *J. Agric. Food Chem.* (1982b), 30, 739; Buttery, et al., *J. Agric. Food Chem.* (1985), 33, 772; and Visser and Ave, *Entomol. Exp. Appl.* (1978), 24, 738), the more important role involving volatiles is probably as insect repellents or deterrents from nonhost plants (Gilbert, et al., supra 1967; Gilbert and Norris, supra 1968; Saxena and Prabha, *J. Entomol. Ser A* (1978); Ryan and Guerin, *Physiol. Entomol.*, (1982), 7, 315; Salama and Saleh, *Angew. Entomol.* (1984), 97, 393; and Khan, et al., supra 1987).

SUMMARY OF THE INVENTION

It is therefore the object of the present invention to develop an insect repellent which is both effective and environmentally safe.

It is further an object of the present invention to develop a means of repelling insects from treated surfaces.

These objects and others are addressed by the present invention which is directed to a method for repelling insects consisting of applying to the insects or the habitat thereof 1-dodecene in an amount effective to repel the insects.

The present invention is also directed to a composition for preventing or deterring insects which comprises as an active ingredient 1-dodecene in an amount effective to repel the insects, and an inert carrier or diluent.

The present invention is further directed to a method for controlling insects on animals and plants comprising applying to the animals or plants or to the locus of the animals or plants 1-dodecene in an amount effective to repel the insects.

The use of 1-dodecene as an insect repellent is advantageous in that it is a natural component of plants. Thus, the insect repellent of the present invention is less likely to be considered either an environmental problem or a safety problem when applied to a plant or animal surface or the habitat thereof. Further, the present invention is easily decomposed, safe and can be applied in reduced amounts when compared to other insect repellents. Therefore, the present invention avoids the problems existent with the use of toxic compounds as repellents while at the same time achieving significantly greater insect repellency than currently available commercial products.

The composition of the present invention can be applied in the same manner as ordinary insect repellents, for example, by the treatment of seeds, seedling culture boxes, spraying stems and leaves of plants and crops, spraying living insects directly, and as topical treatments on animals. Further, the composition of the present invention can be applied to borders of rooms or other areas in order to prevent the ingress of crawling insects. Application to the human or animal skin or hair, clothing, plant surface or shelter (home) walls of an effective amount of such an environmentally safe repellent prevents the insect from even alighting on that surface. The residual effectiveness of the repellent is extended by dispersing such repellent in a non-reactant, non-toxic carrier, e.g., paraffin oil.

The insect repellent of the present invention is known to be effective as a deterrent or controlling mechanism for insect pests of such different orders as: Lepidoptera (e.g., moths and butterflies), Coleoptera (e.g., beetles and weevils), and Orthoptera (e.g., grasshoppers and cockroaches).

Further objects, features and advantages of the present invention will be apparent from the following detailed description when taken in conjunction with the accompanying drawing.

DETAILED DESCRIPTION OF THE INVENTION

Figure 1:
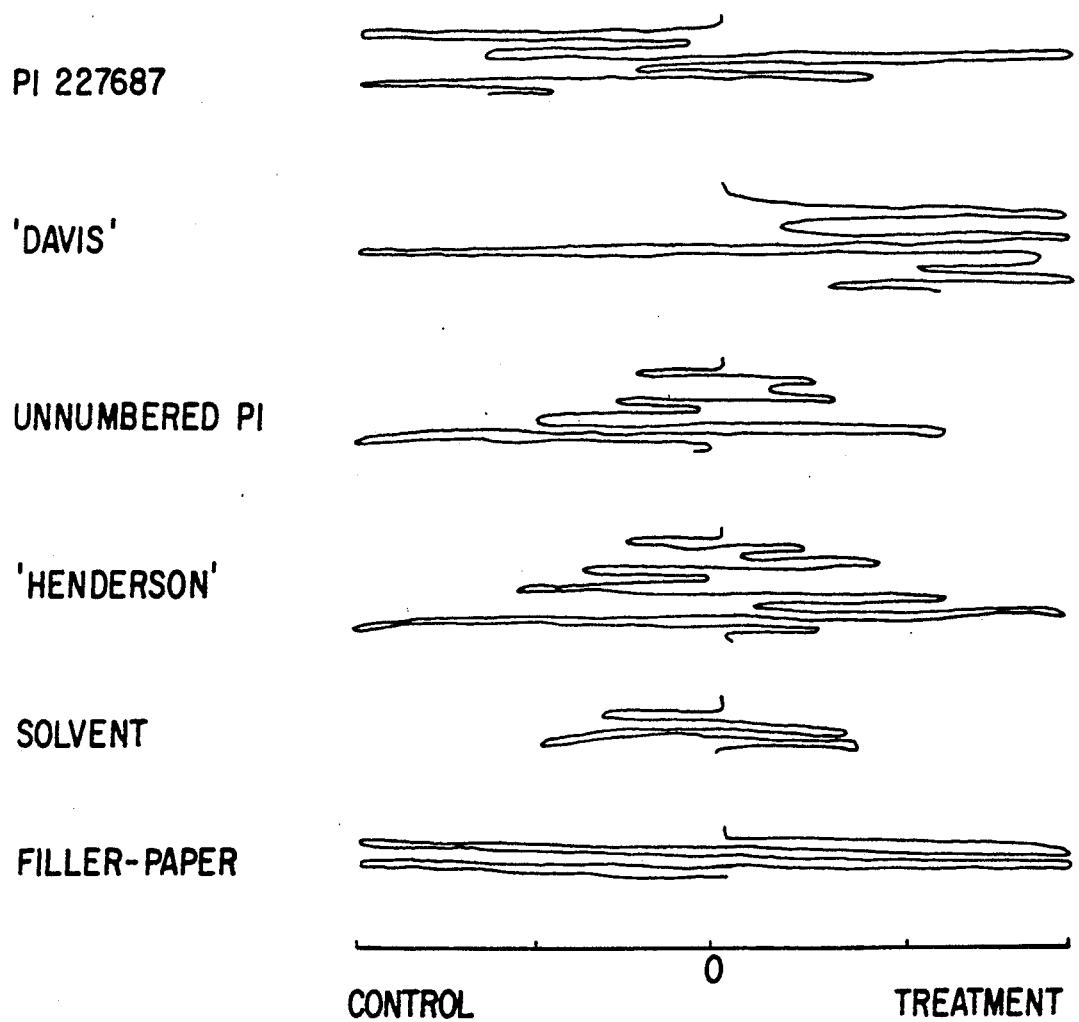
FIG. 1 is an illustration of the tracings of the cabbage looper (*Trichoplusia ni* or *T.ni*) female movements in the bioassay arena in response to plant volatiles (including plant volatiles containing 1-dodecene), or control, as illustrated in examples 1–7.

The present invention relates to 1-dodecene having a chemical formula: $CH_3(CH_2)_9CH=CH_2$, which exhibits excellent insect repelling characteristics. 1-dodecene is a highly volatile 12-carbon, straight chain, environmentally safe hydrocarbon with one unsaturated, i.e., double, carbon-carbon bond. 1-dodecene can be found naturally in certain plants or can be commercially prepared.

In the practice of the present invention, it has been found that 1-dodecene can be dissolved or dispersed in a suitable liquid carrier, or mixed or adsorbed with an appropriate solid carrier to process it into a desired form for use as an insect repellent. As preferable forms of preparation, the composition can be prepared as an emulsifiable concentrate, a wettable powder, and a liquid. These preparations can be prepared, if desired, by methods known to the art, such as by adding emulsifying agents, suspension agents, spreaders, penetrants, wetting agents, tackifiers and stabilizers. Suitable solid carriers include, without limitation, vermiculite, perlite and charcoal.

Suitable examples of the liquid carrier, which may be used in the preparation of the insect repellent of the present invention, include solvent, such as water; alcohols, e.g., methyl alcohol, ethyl alcohol and ethylene glycol; ketones, e.g., acetone and methyl ethyl ketone; ether, e.g., dioxane, tetrahydrofurane and cellosolve; aliphatic and aromatic hydrocarbons, e.g., pentane, hexane, heptane, cyclohexane, petroleum ether, petroleum benzene, benzene, toluene and xylene; and halogenated hyrdrocarbons, e.g., dichloromethane, chloroform, carbon tetrachloride and dichlorlobenzene. The preferred liquid solvent is hexane.

The proportion of 1-dodecene contained in the insect repellent of the present invention, for example, is suitably in the range of 0.015 to 20 volume percent, preferably 0.015 to 1.0 volume percent in the case of a liquid carrier; and 0.015 to 20 volume percent in the case of a solid carrier, preferably from 0.015 to 1.0 volume percent.

An alternative carrier can be in the form of an ointment such as, for example, polyethylene glycol, pectin, polyhydric alcohol, liquid paraffin, i.e., paraffin oil, vegetable oils, white oil, lanolin and resins. Paraffin oil serves nicely because it is non-toxic, non-reactive, protects the dispersed repellent molecules from environmental alteration, slows the release of the repellents into the atmosphere and adheres to skin, hair, fur, clothing and most other treatment surfaces. Any carrier meeting these criteria should be considered to fall within the scope of the claims of this invention. The proportion of the ointment base to the 1-dodecene in the liquid carrier contained in the insect repellent composition of the present invention may range from 40.0 to 60.0 volume percent, preferably from 40.0 to 50.0 volume percent.

An example of a preferred application utilizing the insect repellent of the present invention is as follows: 60 microliters (ul) of hexane (High-Performance Liquid Chromotograpy or HPLC grade) (Aldrich Chemical Co., Inc., Milwaukee, Wis.) which contains 0.015 weight percent 1-dodecene (Aldrich Chemical Co., Inc., Milwaukee, Wis.) was added to 40 ul of No. 30 white oil (American Oil Co., Chicago, Ill.) and applied to 700 square millimeters of surface area to repel insects. The process can be repeated as necessary.

The following examples are presented to illustrate the invention and to facilitate a clearer understanding of the invention. It should be understood, however, that while the examples indicate preferred embodiments, they are not intended to limit the invention in any way. There are changes and modifications within the spirit and scope of the invention which will become apparent to those skilled in the art from this detailed description.

EXAMPLES

The following examples are directed to biological assays of various plant volatiles with respect to a variety of insects. Except where noted, the following parameters apply to all of the examples:

Insects: The insects used in one or more of the examples include the Mexican bean beetle (MBB), (*E. varivestis* Mulsant); the cabbage looper (CL), (*Trichoplusia ni* Hubner), and the cockroach (*Blatella germanica*). The MBB was maintained under greenhouse conditions on snapbean, *Phaseolus vulgaris* L, according to the process described in Liu, et al., *J. Insect Behavior* (1989a) (submitted for publication). The CL was maintained under laboratory conditions on a pinto bean based diet according to a process described in Liu, et al., *E. Entomolo. Exp. Appl.* (1988) 49, 99. The cockroach was maintained under laboratory conditions on a standard dogfood (Gaines ®) diet.

Plants: Volatiles were trapped from freshly detached, fully expanded leaves of V8–V10 soybean or lima bean plants. The soybeans were plant introduction (PI) 227687, reported as relatively resistant to the CL (Leudders and Dickerson, *Crop Sci*, 1977, 17, 395; Kahn, et al., *Environ. Entomol.* 1986a, 15, 803; Kahn, et al., *Entomol. Exp. Appl.*, 1986b, 42, 109), and the Mexican Bean Beetle (Van Duyn, et al., *Crop Sci.*, 1971, 11, 572; Chiang, et al., *Entomol. Exp. Appl.*, 1986, 42, 19; Rufner II, et al., *J. Ecol. Entomol.*, 1986, 1979, 1354); an unnumbered PI soybean plant, and 'Davis', a commercial cultivar, shown to be more susceptible than PI 227687 to the CL (Kahn, et al., supra, 1986a,b) and the MBB (Chiang, et al., supra, 1986). The lima bean variety was 'Henderson', one of the more preferred hosts of CL (Shorey, et al., *Ann. Entomol. Soc. Am.*, 1962, 55, 591) and the MBB (Flander, *Environ. Entomol.*, 1984, 13, 995).

Seeds of PI 227687 and 'Davis' soybeans were obtained from Dr. E. E. Hartwig, Delta Branch Experimental Station, Stoneville, Miss. Seeds of 'Henderson' lima bean were purchased from L. L. Olds Seed Co., Madison, Wis. All seeds were treated with the fungicide Thiram (Science Products Co., Inc., Chicago, Ill.) and germinated in flats of moistened vermiculite in a Percival environmental chamber (Liu and Norris, *Entomol. Exp. Appl.*, 1988, 49, 99–109). Seedlings were transplanted, two plants per pot, at the first leaf (V1) stage.

Plants were grown to the V10 stage in 6-8 weeks in the greenhouse or in 3-6 weeks in the University of Wisconsin Biotron Controlled-Environment facility. All fully expanded trifoliate leaves were then harvested and used immediately for trapping of volatiles.

Tenax® trapping of volatiles: Volatiles were trapped from the fully-expanded leaves of the soybean and lima bean cultivars according to the process disclosed in Liu, et al., supra, 1988, which is incorporated herein by reference. A brief explanation of the Tenax® trapping procedure follows:

Fully-expanded trifoliate leaves (100-g) from soybean or lima bean plants (fresh or frozen as needed) were placed in a modified 1000-ml Pyrex® erlenmeyer-flask chamber with ground-glass openings. The Tenax® trap consisted of a Pyrex® tube packed with 0.17-g Tenax-GLC® (Alltech Associates, Inc., Applied Science Labs, Deerfield, Ill.) as a 0.5-cm diameter by 10-cm long column. Air was first purified and subsequently desiccated by suction through activated charcoal and calcium chloride, respectively, in sequential ground glass-jointed apparatuses. It was next passed into the bottom of the modified erlenmeyer-flask chamber, through the contained 100-g leaves, and then up out of the chamber and through the Tenax® trap. The vacuum air flow was 2000-2500 ml/min, and continued for 24 hours. Trapped volatiles were eluted from the Tenax® with hexane. The volatile-bearing Tenax® was added to 3-ml hexane (HPLC-grade) in a 7-ml screw-capped glass vial, vortexed for two minutes and held at $-10°$ C. for 24 hours. The resultant hexane extractables were filtered, weighted and stored in a screw-capped glass vial at $-10°$ C.

High performance liquid chromatography (HPLC) of soybean and lima bean volatiles. The analysis of the plant volatiles was conducted according to the methods disclosed in Liu, et al., supra, 1988. A brief description of the process follows:

Qualitative and quantitative analyses of the Tenax®-trapped plant volatiles were conducted by HPLC using a prepacked silica column (25-cm long, 4-6-mm diameter, packed with 5-um diameter silica particles (Ultraspere®, Beckman, Inc., Berkeley, Calif.) and a variable UV spectrophotometric detector (Hitachi®, Model 100-40, Japan). The previously described samples of hexane-extracted volatiles were each concentrated 10 times. A sample (20-ul) of such concentrated extractables was then injected for each HPLC analysis. Operating conditions for HPLC were as follows: temperature-ambient; elution phase-hexane; 2-propanol (96:4) (HPLC-grade) for one minute and then 95:5 for 10 minutes; flow rate-1 ml/min; and column pressure, 450 psi. The length of the light wave used for sample detection was 242 nm. Retention time, area and height of each resolved peak were calculated and recorded by a Spectra Physics® Model 4100 computing integrator (Santa Clara, Calif.).

The standard hexane-extracted volatiles were analyzed by capillary gas-liquid chromatography (GLC) with a Hewlett Packard (HP-5890) GLC, using a capillary column (25-m×0.25-mm, open tubular wall coated, OV-17). A gas-liquid chromatography study was conducted with a Finnigan-MAT Model 9610 using a DB-5 capillary column (30-m×0.25-mm, 0.25-micron film thickness) (J and W Scientific) operated in splitless injection mode with helium carrier gas.

From the GLC-MS analysis, the major chemicals included in the volatiles from soybean and lima bean leaves were unsaturated hydrocarbons, alkanals, aliphatic alcohols, aliphatic aldehydes, aliphatic ketones, aliphatic esters and terpenoids. The ratios among components were quite different between species and among cultivars. The more abundant compounds in the 'Davis' volatiles were 4-hexen-1-ol acetate; 2,2-dimethyl hexanal and 2-hexanal; in the PI 227687 volatiles were 3-tetradecene, 4-hexen-1-ol acetate, 2,2-dimethyl hexanal and 1-dodecene; and in the 'Henderson' volatiles were 4-hexen-1-ol acetate, butanoic acid (3-hexenyl ester) and 1-nonen-3-ol.

EXAMPLE 1

Example 1 was designed to determine the effect of PI 227687 soybean volatiles from fresh leaves on the cabbage looper (CL). Behaviorial responses of CL to PI 227687 volatiles from fresh leaves were determined according to the method described in Khan et al., supra, 1987 and Weiss & D. M. Norris, Exp. Appl., 1989 (submitted for publication), which are incorporated herein by reference for a description of the experimental procedure. Basically, the responses were assayed in a horizontal 3-cm interior diameter (i.d.) by 15-cm long cylindrical glass-tube arena, which was open at both ends and had a center 15-mm i.d. sidewall opening for introduction of the assay insect. The assay arena was divided into quadrants; the control end was always designated 1, and the treatment end, quadrant 4. The opening at each end of the cylindrical arena was covered by 36-gauge plastic screen (Chicopee Products, Inc., Cornelia, Ga.).

Each chemical treatment consisted of 40 ul of standardized hexane extractables from the Tenax® trappings plus 50 ul of No. 30 white oil, U.S.P. applied to a 30-cm diameter filter paper (Whatman #1) disc. The combination of hexane and the white oil served as the solvent-dispersant control. A filter-paper disc bearing the chemical treatment version and one bearing the solvent control were positioned oppositely outside the two screened ends of the arena; and each positioned disc was secured by a plastic cup (3.5-cm diameter). Each securing cup was uniformly perforated with 6 (1-cm diameter) holes in its bottom and side to allow for air flow.

Bioassays were conducted under the environmental conditions of $23°\pm2°$ C., $60\pm5\%$ relative humidity and with lighting provided by two Sylvania® cool white 34-watt fluorescent bulbs.

A single, mated, gravid CL female, 4 to 6-days old, was placed into the center of the otherwise-prepared tubular assay arena through the centered side opening, which then was plugged with a cork. Using a stopwatch, moth orientation and movement were recorded in seconds, according to quadrant, for 5 minutes; touching either end screen was also noted. After each replicate assay, the cylindrical arena was rotated 180° to correct for effects of otherwise unrecognized stimuli. Six or more replicate assays were conducted for each treatment. A trace of each moth's approximate movements is illustrated in FIG. 1.

The results indicate that hexane extractables eluted from Tenax® trappings of volatiles from the relatively insect resistant fresh PI 2276878 soybean leaves were significantly repellent to CL gravid females (P less than 0.01; t-test) as compared to a solvent (hexane plus white oil) control as illustrated in Table 1 below.

EXAMPLE 2

Example 2 was designed to determine the effect of PI 27687 soybean volatiles from frozen leaves on CL gravid females. The procedure of Example 1 was followed precisely with the exception that frozen leaves were used.

The results indicate that hexane extractables eluted from Tenax ® trappings of volatiles from the relatively insect resistant frozen PI 227687 soybean leaves were significantly repellent to CL gravid females (P less than 0.05; t-test) as compared to a solvent (hexane plus white oil) control as illustrated in Table 1 below.

EXAMPLE 3

Example 3 was designed to determine the effect of 'Davis' soybean volatiles from fresh leaves on CL. The procedure of Example 1 was followed in Example 3.

The results indicate that hexane extractables from fresh 'Davis' leaves were highly attractive to CL insects (P less than 0.01; t-test) as illustrated in Table 1 below.

EXAMPLE 6

Example 6 was designed to determine the effect of 'Henderson' lima bean volatiles from fresh leaves on CL. The procedure of example 1 was followed in example 6.

The results indicate that the volatiles from fresh Henderson lima bean leaves were "odor neutral" to the insect (P less than 0.05; t-test), as illustrated in Table 1 below. The 'Henderson' lima bean volatiles behaved similarly to the controls.

EXAMPLE 7

Example 7 was designed to determine the effect of 'Henderson' lima bean volatiles from frozen leaves on CL. The experimental procedure of example 1 was followed with respect to Example 7.

The results indicate that the volatiles from frozen 'Henderson' lima bean leaves were "odor neutral" to the CL (P less than 0.05; t-test), as illustrated below in Table 1. The results here were similar to the results of the controls.

TABLE 1

| | | Mean, and percentage of total, seconds which CL spent in each half of the assay arena[a] | | | | |
|---|---|---|---|---|---|---|
| | Example[b] | Control (c) Side | % | Treatment (T) Side | % | Difference[c] T − C (%) |
| 1 | PI227687 (fresh) | 217.0 | 72.3 | 83.0 | 27.7 | −134.0 (−44.6)** |
| 2 | PI227687 (frozen) | 188.3 | 62.8 | 111.7 | 37.2 | −76.6 (−25.6)* |
| 3 | 'Davis' (fresh) | 63.5 | 21.2 | 236.5 | 78.8 | +173.0 (+57.6)** |
| 4 | 'Davis' (frozen) | 89.2 | 29.7 | 210.8 | 70.3 | +121.6 (+40.6)** |
| 5 | Unnumbered PI (frozen) | 177.0 | 59.0 | 123.0 | 41.0 | −54.0 (−18.0) NS |
| 6 | 'Henderson' (fresh) | 154.0 | 51.3 | 146.0 | 48.7 | −8.0 (−2.6) NS |
| 7 | 'Henderson' (frozen) | 159.5 | 53.2 | 140.5 | 46.8 | −19.0 (−6.4) NS |
| | Solvent (control) | 152.5 | 50.8 | 147.5 | 49.2 | −5.0 (−1.6) NS |
| | Filter paper (control) | 155.5 | 51.8 | 144.5 | 48.2 | −11.0 (−3.6) NS |

[a]Data are averages of six or more replications; in each, one female adult CL was assayed for 300 sec (5 min).
[b]Treatment consisted of 40 ul of given volatile hexane extractables, obtained by Tenax ® trapping, plus 50 ul white oil (1–7); solvent control was 40 ul hexane plus 50 ul white oil.
[c]Differences between means followed by two asterisks are significantly different at P = less than 0.01 level (t-test); by a single asterisk, at P = less than 0.05 level; NS, not significant.

EXAMPLE 4

Example 4 was designed to determine the effect of 'Davis' soybean volatiles from frozen leaves on CL. The procedure of Example 1 was followed in Example 4.

The results indicate that the hexane extractables from frozen 'Davis' leaves were highly attractive to CL insects (P less than 0.01; t-test) as illustrated in Table 1 below.

EXAMPLE 5

Example 5 was designed to determine the effect of the unnumbered PI soybean volatiles from frozen leaves on CL. The procedure of example 1 was followed in Example 5.

The results indicate that volatiles from the unnumbered PI soybean leaves were behaviorally neutral (neither attracting nor repelling) to the CL as illustrated in Table 1 below. The behavior of the CL was similar for unnumbered PI soybean volatiles and controls.

EXAMPLE 8

Example 8 was designed to determine the effect of commercial dodecene on CL. A composition comprised of 0.015 volume percent 1-dodecene (Aldridge Chemical Co., Inc., Milwaukee, Wis.) in hexane was prepared and utilized according to the experimental procedure described in Example 1. Doses are shown in Table 2. The results indicate a very strong repellency to CL female adults as illustrated in Table 2 below.

TABLE 2

| Bioassay of commercial dodecene against CL females adults[a] | | | | | | |
|---|---|---|---|---|---|---|
| Treatment Chemical | Dose (ul) | C-Side | % | T-Side | % | Difference T − C (%) |
| Dodecene (0.015%) | 20 | 161.9 | 54.0 | 138.1 | 46.0 | −23.8 (−8.0) NS |
| | 40 | 178.0 | 59.3 | 122.0 | 40.7 | −56.0 (−18.6)* |
| | 60 | 195.9 | 65.3 | 104.1 | 34.7 | −91.8 (−30.6)** |

[a]Data are averages of ten replicates; otherwise bioassay and data collection and analysis are the same as in Table 1.

With reference to FIG. 1, it can be seen that the CL gravid females spent most of their time in the middle of the cylindrical area, i.e., quadrant 2 or 3 when the solvent control was positioned at both ends. With a filter-paper control at each end, the moths stayed longer at the ends, i.e., in quadrant 1 or 4, and frequently touched the screen. When the mean time was calculated for half of the assay arena, the insects spent equal time (P greater than 0.5; t-test) in each half as shown in Table 1. CL adults stayed much longer in the treatment side (quadrant 3 or 4, or on the screen of the treatment end) than in the control side (quadrant 1 or 2, or on the screen at the control end) in the presence of 'Davis' volatiles, either from fresh or frozen leaves. When the PI 227287 volatiles were present, moths showed the opposite behavior. They avoided the treatment end, approached the control end and stayed much longer. When the unnumbered PI volatiles were present, the insect spent a numerically but statistically insignificant greater time on the control versus treated side. With 'Henderson' lima bean volatiles, either fresh or frozen leaves, CL adults spent the most time in the middle half, i.e., quadrant 2 and 3, of the assay arena. These latter results were similar to those for paired solvent controls. Thus, the tracings on FIG. 1 indicate that CL female adults approached the volatiles of 'Davis' soybeans, avoided the odors of PI 227687 soybeans, and shifted (non-significantly) to the control side when the extractables of the unnumbered PI soybean were presented. The CL female adults also were neither attracted nor repelled by the 'Henderson' lima bean volatiles.

EXAMPLE 9

Example 9 was designed to determine the effect of soybeans volatiles from fresh leaves of PI 227687 on the Mexican bean beetle (MBB). The experimental procedure of Example 1 was followed in to Example 9.

The results indicate that the Tenax ®-trapped hexane-extractable volatiles from the relatively insect-resistant PI 227687 soybean were significantly repellent the MBB adults (P less than 0.05; t-test) as compared to a solvent (hexane plus white-oil) control, as illustrated in Table 3 below.

EXAMPLE 10

Example 10 was designed to determine the effect of 'Davis' soybean volatiles from fresh leaves on MBB. The experimental procedure of Example 1 was followed with respect to Example 10.

The results indicate that the volatiles from the relatively less insect-resistant 'Davis' soybean leaves were highly attractive to the MBB (P less than 0.05; t-test) as illustrated in Table 3 below.

EXAMPLE 11

Example 11 was designed to determine the effect of 'Henderson' soybean volatiles from fresh leaves on MBB. The experimental procedure of Example 1 was followed in Example 11.

The results indicate that the odors from the insect-preferred 'Henderson' lima bean leaves were neutral, i.e., neither attractive or repellent to the MBB (P less than 0.05; t-test), as illustrated in Table 3 below.

TABLE 3

Responses of MBB Female Adults to Volatiles from Soybean and Lima Bean Leaves[a]

| Example | Treatment | MBB[b] c-side | t-side | t − c[c] |
|---|---|---|---|---|
| 9 | PI 227687 | 60.9 | 39.1 | −21.8* |
| 10 | Davis | 39.7 | 60.3 | +20.6* |
| 11 | Henderson | 49.4 | 50.6 | +1.2 NS |
|  | Solvent (control) | 48.9 | 51.1 | +2.2 NS |
|  | Filter Paper (control) | 52.5 | 47.5 | −5.0 NS |

[a] Data are the mean times, as percentages, that insects spent in each half (side) (i.e., c = control and t = treated) of the assay arena and averages of 6-18 replications.
[b] In each replication one female MBB was assayed for 1800 s (30 min).
[c] Differences between means followed by a single asterisk are significantly different at P = 0.05 level (t = test); double asterisks, P = 0.01 level; NS, not significant.

EXAMPLE 12

Example 12 was designed to determine the differences in responses by a single male adult cockroach (*Blatella germanica*) between 1-dodecene and DEET. German cockroaches (*Blatella germanica*) are among the most difficult species of pest or vector arthropods to repel from a surface or volume of space. Single adult male German cockroaches were given a choice, using a standardized, open ended glass tube behavioral arena which was detailed by Norris, et al., (eds.), *Endocrinological Frontiers in Physiological Insect Ecology*, (1988), between an indicated dosage of a candidate repellent on a standard filter paper versus untreated filter paper. Each bioassay was run for 15 minutes during which the location of the single arthropod cockroach was continually noted and its detailed movements in the arena were recorded in hundreds of seconds using a trained observer with a digital stopwatch. Besides recording which quadrant of the bilaterally symmetrical glass tube arena the observed insect was in per millisecond; and time spent on the repellent-treated or control filter papers over the opposing, otherwise open ends of the tube arena was likewise recorded.

The results are illustrated on Table 4 as follows:

TABLE 4

Behavioral Responses by a Single Male Adult *Blattella germanica* Cockroach between the Indicated Treatment versus Control.

| Specific Treatment | Replication | % Time Spent Treatment | Control |
|---|---|---|---|
| N,N-Diethyl meta-toluamide (DEET) (71.25%) (75 ul) | 1 | 84.4 | 15.6 |
|  | 2 | 29.6 | 70.4 |
|  | 3 | 37.0 | 63.0 |
|  | 4 | 0.0 | 100.0 |
|  | 5 | 26.8 | 73.2 |
|  | 6 | 7.7 | 92.3 |
|  | 7 | 41.6 | 58.4 |
|  | 8 | 67.5 | 32.5 |
|  | x̄ | 36.8 | 63.2* |
| 1-Dodecene (1%) (75 ul) | 1 | 65.8 | 34.2 |
|  | 2 | 19.8 | 80.2 |
|  | 3 | 46.1 | 53.9 |
|  | 4 | 26.0 | 74.0 |
|  | 5 | 12.7 | 87.3 |
|  | 6 | 23.2 | 76.8 |
|  | 7 | 68.9 | 31.1 |
|  | 8 | 20.3 | 79.7 |
|  | x̄ | 35.4 | 64.6* |

*Difference between the mean for effectiveness of 1% 1-dodecene versus 71.25% DEET is not significant at the P less than 0.05 level.

Behavior tests clearly show that treatment of the standardized area of the filter paper disk with 75 ul of 1% 1-dodecene was equal in repulsion of the single male adult German cockroach to such treatment with 75 ul of 71.25% N,N-diethyl meta-toluamide (DEET). The observed results would indicate that in these specific experiments 1-dodecene was about 70 times as repellent as DEET, the currently most widely used active ingredient in commercial insect repellents.

The results of Examples 1–11 indicate that the relatively wild, i.e., relatively non-human altered, PI 227687 soybean is highly repellent and resistant to CL, MBB and the cockroach, while the more human-created 'Davis' soybean is attractive and relatively more susceptible to these insects. The numbered PI soybean was more suitable than 'Davis' as a sole host for CL; even though its volatiles, at most, are slightly repellent, rather than strongly attractive, as are those of 'Davis'. Odors from 'Henderson' lima bean, one of the more preferred host plants of both CL and MBB, had no apparent influence on either insects behavior.

The major compounds in PI 227687 volatiles, 3-tetradecene and 1-dodecene, are highly reponsible for the insect repellency of PI 227687; and are absent in 'Davis' odors. Thus, the attraction of 'Davis' odors to the assayed insects is apparently attributable to the absence of tetrodecene and dodecene.

It is understood that the invention is not confined to the particular construction and arrangement herein illustrated and described, but embraces such modified forms thereof as come within the scope of the following claims.

What is claimed is:

1. A method for repelling insects consisting of applying to the insects or habitat thereof 1-dodecene in an amount effective to repel the insects.

2. The method of claim 1, wherein the insects are selected from the insect orders consisting of Lepidoptera, Coleoptera and Orthoptera.

3. The method of claim 1, wherein 1-dodecene is dispersed in a solid carrier.

4. The method of claim 3, wherein 1-dodecene is present in the solid carrier in an amount between about 0.015 and about 20 volume percent.

5. The method of claim 1, wherein 1-dodecene is dispersed in a liquid carrier selected from the group consisting of alcohols, ketones, ethers, aliphatic hydrocarbons, aromatic hydrocarbons, and halogenated hydrocarbons.

6. The method of claim 5, wherein the liquid carrier is hexane.

7. The method of claim 5, wherein 1-dodecene is present in the liquid carrier in an amount between about 0.015 and about 20 volume percent.

8. The method of claim 5, wherein water can be combined with the liquid carrier.

9. The method of claim 1, wherein 1-dodecene is dispersed in an ointment-based carrier selected from the group consisting of polyethylene glycol, pectin, polyhydric alcohol, liquid paraffin, vegetable oil, white oil, lanolin and resins.

10. The method of claim 9, wherein 1-dodecene is present in the ointment-based carrier in an amount between about 0.015 and about 20 volume percent.

11. The method of claim 9, wherein the 1-dodecene is present in the ointment-based carrier in an amount between about 0.015 and about 1.0 volume percent.

12. A method for repelling insects consisting of applying to the insects or habitat thereof 1-dodecene, wherein the 1-dodecene is present in a liquid carrier in an amount between about 0.015 and about 1.0 volume percent.

13. The method of claim 12, wherein the liquid carrier is selected from the group consisting of alcohols, ketones, ethers, aliphatic hydrocarbons, aromatic hydrocarbons and halogenated hydrocarbons.

14. The method of claim 12, wherein the liquid carrier is hexane.

15. The method of claim 13, wherein water can be combined with the liquid carrier.

16. An insect repellent composition for preventing or deterring insects which comprises as an active ingredient 1-dodecene in an amount effective to repel the insects, an inert carrier suitable for insect repellent compositions, and an emulsifying agent.

17. The composition of claim 16, wherein the inert carrier is selected from the group consisting of liquid carriers, solid carriers and ointment-based carriers.

18. The composition of claim 16, wherein 1-dodecene is present in a solid carrier in an amount between about 0.015 and about 20 volume percent.

19. The composition of claim 16, wherein the inert carrier is a liquid carrier selected from the group consisting of alcohols, ketones, ethers, aliphatic hydrocarbons, aromatic hydrocarbons, and halogenated hydrocarbons.

20. The composition of claim 19, wherein water can be combined with the liquid carrier.

21. The composition of claim 16, wherein the carrier is hexane.

22. The composition of claim 16 wherein 1-dodecene is present in a liquid carrier in an amount between about 0.015 and about 20 volume percent.

23. The composition of claim 16, wherein 1-dodecene is present in a liquid carrier in an amount between about 0.015 and about 1.0 volume percent.

24. The composition of claim 16 wherein the inert carrier is an ointment-based carrier selected from the group consisting of polyethylene glycol, pectin, polyhydric alcohol, liquid paraffin, vegetable oil, white oil, lanolin and resins.

* * * * *